United States Patent [19]
Lockett et al.

[11] Patent Number: 5,854,224
[45] Date of Patent: Dec. 29, 1998

[54] COMPOSITION AND METHOD FOR DELIVERY OF NUCLEIC ACIDS

[75] Inventors: Trevor John Lockett, Denistone; Robert George Whittaker, West Pymble; Fiona Helen Cameron, Lindfield; Minoo Jalili Moghaddam, Killara; Simon MacEwan Carroll, Heidelberg, all of Australia

[73] Assignee: Commonwealth Scientific and Industrial Research Organisation, Campbell, Australia

[21] Appl. No.: 720,200

[22] Filed: Sep. 25, 1996

[30] Foreign Application Priority Data

Jan. 5, 1996 [AU] Australia ............... PN 7416

[51] Int. Cl.$^6$ ............... A01N 43/04; C07C 69/52; C07C 53/00; C07F 9/02; C12Q 1/68

[52] U.S. Cl. ............... 514/44; 435/6; 554/80; 554/224; 560/155; 560/252; 560/224

[58] Field of Search ............... 435/6; 514/44; 554/80, 224; 560/155, 252, 224

[56] References Cited

U.S. PATENT DOCUMENTS 5,264,618  11/1993  Felgner et al. ............... 560/224
5,329,029   7/1994  Wan ............... 554/80

OTHER PUBLICATIONS

Newkome et al. "Polytryptophane terminated dendritic macromolecules" Tetrahedron: Asymmetry, vol. 2, pp. 957–960, 1991.

*Primary Examiner*—Ardin H. Marschel
*Assistant Examiner*—Jezia Riley
*Attorney, Agent, or Firm*—McDermott, Will & Emery

[57] ABSTRACT

The present invention provides a method for introducing nucleic acids into cells. The method involves exposing the cells to a compound having the formula

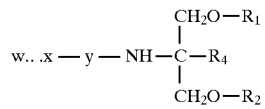

in which:

w is a nucleic acid x is a non-amino acid or non-peptide nucleic acid binding group y is a spacer having a chain length equivalent to 1–30 carbon-carbon single covalent bonds or is absent $R_4$ is H or halogen or $CH_2O$—$R_3$; and $R_1$, $R_2$ and $R_3$ are the same or different and are either hydrogen, methyl, ethyl, alkyl, alkenyl, hydroxylated alkyl, hydroxylated alkenyl groups or ether containing alkyl, alkenyl, hydroxylated alkyl or hydroxylated alkenyl groups optionally being an acyl group having a carbon chain length equivalent to 3–24 carbon atoms saturated or unsaturated, with the proviso that at least one of $R_1$, $R_2$ or $R_3$ includes a group having a carbon chain of 3–24 carbon atoms saturated or unsaturated, or to a compound having the formula:

w . . . y—y—NH—$CH_2$—$CH_2O$—$R_5$ in which:

w is a nucleic acid x is a non-amino acid or non-peptide nucleic acid binding group y is a space having a chain length equivalent to 1–30 carbon-carbon single covalent bonds or is absent $R_5$ is alkyl, alkenyl, hydroxylated alkyl, hydroxylated alkenyl group or ether containing alkyl, alkenyl, hydroxylated alkyl or hydroxylated alkenyl group optionally being an acyl group having a carbon chain length equivalent to 3–24 carbon atoms saturated or unsaturated, with the proviso that $R_5$ includes a group having a carbon chain of 3–24 carbon atoms saturated or unsaturated.

The invention also relates to these compounds.

62 Claims, No Drawings

COMPOSITION AND METHOD FOR DELIVERY OF NUCLEIC ACIDS

COMPOSITION AND METHOD FOR DELIVERY OF NUCLEIC ACIDS

The present invention relates to a method of introducing compounds, in particular nucleic acids, into cells. Further, the present invention relates to compositions for use in this method.

There are a number of situations in which it is desirable to deliver specific compounds into cells. One of these applications is the transfection of eucaryotic cells with DNA. This is currently done using various commercial lipofecting agents such as "Transfectam" (Promega) and "Lipofectin" (BRL), by using calcium phosphate mediated transfection or by electroporation of cells.

The ability to deliver nucleic acid based compounds to cells also has application in drug delivery. Delivery of drugs into cells or tissues in association with a compound of the formula described below will change parameters such as the duration of drug action (e.g. slow release or sustained action), the amount of drug required or the mode of delivery. The delivery of drugs using compounds variant within the parameters described below should also enable more specific targeting of drug delivery both within cells and whole organisms.

As disclosed in the present applicants' co-pending International patent application No. PCT/AU95/00505 (the disclosure or which is incorporated herein by cross-reference), nucleic acid may be introduced into a cell by exposing the cell to a compound of the formula:

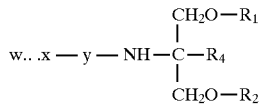

in which:
w is a nucleic acid
x is an amino acid or peptide
y is a spacer having a chain length equivalent to 1–20 carbon atoms or is absent
$R_4$ is H or $CH_2O$—$R_3$, and $R_1$, $R_2$ and $R_3$ are the same or different and are either hydrogen, methyl, ethyl, hydroxyl or acyl groups derived from a fatty acid having a carbon chain of 3–24 carbon atoms saturated or unsaturated with the proviso that at least one of $R_1$, $R_2$ and $R_3$ is an acyl group derived from a fatty acid.

The present inventors now believe that it is possible to introduce nucleic acid into a cell using similar compounds but in which the nature of "x" is varied.

Accordingly, in the first aspect the present invention consists in the method of introducing nucleic acid into a cell comprising exposing the cell to a compound having the formula:

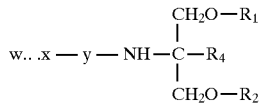

in which:
w is a nucleic acid
x is a non-amino acid or non-peptide nucleic acid binding group
y is a spacer having a chain length equivalent to 1–30 carbon-carbon single covalent bonds or is absent
$R_4$ is H or halogen or $CH_2O$—$R_3$; and $R_1$, $R_2$ and $R_3$ are the same or different and are either hydrogen, methyl, ethyl, alkyl, alkenyl, hydroxylated alkyl, hydroxylated alkenyl groups or ether containing alkyl, alkenyl, hydroxylated alkyl or hydroxylated alkenyl groups, optionally being an acyl group derived from a fatty acid having a carbon chain length equivalent to 3–24 carbon atoms saturated or unsaturated, with the proviso that at least one of $R_1$, $R_2$ or $R_3$ includes a group having a carbon chain of 3–24 carbon atoms saturated or unsaturated.

In a second aspect the present invention consists of a compound for the use of introducing nucleic acid into a cell, the compound having the formula:

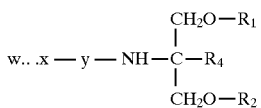

in which:
w is a nucleic acid
x is a non-amino acid or non-peptide nucleic acid binding group
y is a spacer having a chain length equivalent to 1–30 carbon-carbon single covalent bonds or is absent
$R_4$ is H or halogen or $CH_2O$—$R_3$; and $R_1$, $R_2$ and $R_3$ are the same or different and are either hydrogen, methyl, ethyl, alkyl, alkenyl, hydroxylated alkyl, hydroxylated alkenyl groups or ether containing alkyl, alkenyl, hydroxylated alkyl or hydroxylated alkenyl groups, optionally being an acyl group derived from a fatty acid having a carbon chain length equivalent to 3–24 carbon atoms saturated or unsaturated, with the proviso that at least one of $R_1$, $R_2$ or $R_3$ includes a group having a carbon chain of 3–24 carbon atoms saturated or unsaturated.

The nucleic acid may be DNA, RNA or oligonucleotides of either DNA or RNA, modified oligonucleotides or a combination of these.

The nucleic acid "w" may associate with the non-amino acid or non-peptide nucleic acid binding group in any manner such as covalent bonding, ionic interaction, hydrogen bonding, base pairing etc. It is currently preferred, however, that the association between "w" and "x" is an ionic interaction or hydrogen bonding or triplex formation.

The nucleic acid binding group "x" may be an anion or polyanion of any length. In this embodiment, the nucleic acid binding group will typically possess an overall positive charge to attract and hold the nucleic acid by ionic interaction. For example, the nucleic acid binding group may be a polyamine such as spermine, a polyimine or a dendrimer.

The nucleic acid binding group "x" or the spacer "y" may also include functional domains that facilitate cellular targeting or subcellular localisation e.g. sugars, receptor ligands, polysaccharides or peptides (such as nuclear localisation signals, antibodies or derivatives thereof e.g. FABs or SCFVs). Such functional domains may be included in tandem or on a bifurcating structure, as homo or heterodimers.

In another embodiment of the present invention the nucleic acid binding group "x" is itself an oligonucleotide of either DNA or RNA, a modified oligonucleotide or a combination of these or a molecule of PNA capable of binding the nucleic acid "w" through base pairing, triple helix formation or similar interactions.

Nucleotides are the building blocks of nucleic acids. In their most abundant natural forms, they consist of a pentose sugar (ribose or 2-deoxyribose) with a hydrophobic nitrogenous base (a purine, Adenine or Guanine, or a pyrimidine, Thymine (Uracil in ribonucleotides) or Cytosine) covalently attached to the 1' carbon and phosphoric acid esterified to the free hydroxyl group on the 5' carbon of the pentose sugar. Nucleic acids are polymer of successive nucleotide units in which one nucleotide is linked to the next by a phosphodiester bridge between the 3'-hydroxyl group of the pentose moiety of one nucleotide and the 5'-hydroxyl of the pentose moiety of the next. While there are two main sugars found in nucleic acids, in nature any particular nucleic acid does not contain both of these at the same time. Thus there are two kinds of nucleic acid, ribonucleic acid (RNA) and deoxyribonucleic acid (DNA). Furthermore, the covalent backbone of a nucleic acid consist of alternating pentose and phosphoric acid groups and provides a molecular scaffold with a defined polarity from which the side-chain purine and pyrimidine bases are displayed. It is the sequence of the bases as they occur along this polarised polymer that endows nucleic acids with their special properties.

The property of nucleic acids (or more specifically the individual bases) that is crucial to this embodiment of the present invention is that the bases can pair with each other through hydrogen bonding. In general Adenine base pairs with Thymine (Uracil in RNA) and Guanine with Cytosine (complementary base pairing). Where base pairing occurs between bases on different nucleic acid molecules, the appropriate interactions between bases occur if the polarity of the sugar/phosphate backbones from which the bases are displayed are in opposite orientations in the two strands. The hydrogen bonding that occurs in these base interactions provides a force that can potentiate and stabilise associations between different nucleic acid molecules. The strength of these associations depends upon the degree of complementarity of the base sequences of the interacting strands when they are aligned with opposite polarities. In an aqueous solvent, complementary strands of nucleic acid associate to form a double helix or duplex with the sugar phosphate backbone in contact with the solvent and the hydrophobic bases stacking in the middle of the helix. Thus, in addition to the force of hydrogen bonding between all the composite base pairs, the London dispersion forces and hydrophobic effects caused by interactions between the stacked bases further serve to stabilise the association between complementary strands of nucleic acid. (Saenger, W. (1984) Principles of nucleic acid structure. Springer-Verlag (New York). While Adenine-Thymine (Uracil) and Guanine-Cytosine base pairs are the most common in nature, other base pairings can occur and can still contribute significantly to stabilisation of a duplex (Saenger (1984) ibid.).

The development of chemical methods for the synthesis of nucleic acids has made it possible to produce chimaeric DNA/RNA molecules. In addition it has provided the means of synthesising nucleic acids with altered bases and sugars and phosphate groups which can often lead to the improved stability of these molecules in biological fluids (see "Oligonucleotides and analogues, a practical approach" (1991) IRL Press at Oxford University Press, Oxford, Eckstein F. ed.). In addition modified amino acids, in which amino acid side chains are replaced by the purine and pyrimidine bases found in nucleic acids, can also be synthesised (Egholm, M., Buchardt, O., Nielsen, P. E. and Berg, R. H. (1992), J. Am. Chem. Soc. 114 1895–1897; Egholm, M., P. E. Nielsen, O. Buchardt and R. H. Berg. (1992). J. Am. Chem. Soc. 114, 9677–9678). These protein-nucleic acid molecules or PNA can also associate with a nucleic acid of complementary sequence through base pairing (Nielsen, P. E., Egholm, M., Berg, R. H. and Buchardt, O. (1993). Anticancer Drug Des. 8, 53–63; Hanvey, J. C., Peffer, N. J., Bisi, J. E., Thomson, S. A., Cadilla, R., Josey, J. A., Ricca, D. J., Hassman, C. F., Bonham, M. A., Au, K. G. et al. (1992). Science. 258, 1481–5; Egholm, M., Buchardt, O., Christensen, L., Behrens, C., Freier, S. M., Driver, D. A., Berg, R. H., Kim, S. K., Norden, B. and Nielsen, P. E. (1993). Nature. 365 566–8; Nielsen, P. E., Egholm, M., Berg, R. H. and Buchardt, O. (1993). Nucleic Acids Res. 21, 197–200).

While the interactions between the nucleic acid, modified nucleic acid and PNA species described above all involve interactions between two molecules, nucleic acids consisting of homo pyrimidine tracts can associate with double stranded nucleic acid carrying a region of duplex comprising complementary sequences of homo purine and the same homo pyrimidine tract. In such a ternary complex, the homo purine homo pyrimidine tracts of the initial duplex remain antiparallel and Watson-Crick base paired in the normal manner, while the invading homo pyrimidine strand fits into the deep major groove of this double helix and is involved in Hoogsteen-type base pairing with the bases of the polypurine containing strand. In such triple helical structures, the polarity of the invading polypyrimidine strand is the same as that of the polypurine strand (In Saenger, W. (1984) Principles of nucleic acid structure. Springer-Verlag (New York). The nucleic acids contributing to the triplex can be RNA or DNA although there is some evidence to suggest that an RNA third strand may bind more strongly to a DNA/DNA duplex than the corresponding DNA third strand (Roberts, R. W. and Crothers, D. M. (1992) Science 258: 1463–1466). Modified oligonucleotides may also be used as the third strand e.g. 4'-thio-RNA (Leydier C., Bellon, L. Barascut, J-L., Morvan, F., Rayner, B. and Imbach, J-L. (1995) Antisense Res. and Dev. 5: 167–174). Triplexes have also been formed in which the third strand is a polypurine-containing nucleic acid (Porumb, H., Dagneaux, C., Letellier, R., Malvy, C. and Taillandier, E. (1994) Gener 1494: 101–107). In this example the complex was based on reverse Hoogsteen G(GC) and A(AT) triplets (the pairs in parenthesis indicating the Watson-Crick base pairs present in the initial duplex) with anti orientations of the bases and all the strands having S-type sugar conformations.

From the forgoing discussion it will be apparent that base pairing in a variety of forms can facilitate the association of two molecules of nucleic acid or a molecule of a nucleic acid and another of PNA or, in special circumstances, a single stranded nucleic acid with a nucleic acid duplex to form a triple helical structure. In all cases, it is well known that binding affinities are dependent on the length of homology, the level of complementarity, the base composition of the interacting sequences and the pH and ionic strength of the solution (for double stranded interactions see Britten, R. J. and Davidson, E. H. (1985) in "Nucleic Acid Hybridisation: a Practical Approach", IRL Press Oxford. Washington D.C., Hames, B. D. and Higgins, S. J. eds; Sambrook, J., Fritsch, E. F. and Maniatis, T. (1989) "Molecular Cloning, A Laboratory Manual", Cold Spring Harbor Laboratory Press, Nolan, C. ed.: for triplexes see Rougee, M., Faucon, B., Mergny, J. L., Barcelo, F., Giovannangeli, C., Garestier, T. and Helene, C. (1992) Biochemistry 31: 9269–9278; Singleton, S. F. and Dervan, P. B. (1992) Biochemistry 31: 10995–11003; Singleton, S. F. and Dervan, P. B. (1992) J. Am. Chem. Soc. 114: 6957–6965; for nucleic acid/PNA see Egholm, M., Buchardt, O., Christensen, L., Behrens, C., Freier, S. M., Driver, D. A., Berg, R. H., Kim, S. K., Norden, B. and Nielsen, P. E. (1993). Nature. 365: 566–8; Egholm, M., Buchardt, O., Nielsen, P. E. and Berg, R. H. (1992). J.

Am. Chem. Soc. 114: 1895–1897). Thus in the current invention, a single stranded nucleic acid or PNA "x" group with defined sequence properties could function as a nucleic acid binding domain in the compound either by base pairing to a complementary single stranded region on or by forming a triplex with a suitable double stranded sequence in the nucleic acid to be delivered.

Another example of nucleic acid binding groups are polyamides as exemplified by the antibiotics distamycin and netropsin. The repeating amide of distamycin is formed from an aromatic carboxylic acid and an aromatic amine combined to form a crescent shaped tripeptide. This tripeptide binds in the minor groove of double stranded DNA at sites of five successive AT base pairs but shows no appreciable binding to single stranded DNA or RNA. Binding of the antibiotic to the double stranded DNA is believed to be stabilised through a combination of hydrogen bonding to the base pairs, van der Waal's contacts and electostatic forces (Coll, M., Frederick, C. A., Wang A. H. and Rich, A (1987) Proc. Natl. Acad. Sci. U.S.A. 84: 8385–8389). Although both netropsin and distamycin bind as monomers in the minor groove, at high concentration distamycin can bind as a dimer (Pelton, J. G. and Wemmer, D. E. (1989) Proc. Natl. Acad. Sci. U.S.A. 86: 5723–5727). Based on these observations, structurally related polyamides containing N-methylimidazole and N-methylpyrrole amino acids have been synthesised and shown to combine as antiparallel side-by-side dimeric complexes with the minor groove of DNA (Mrksich, M., Wade, W. S., Dwyer, T. J., Geierstranger, B. H., Wemmer, D. E. and Dervan P. B. (1992) Proc. Natl. Acad. Sci. U.S.A. 89: 7586–7590). Covalently linking such polyamide heterodimers and homodimers has led to the design of ligands with both increased affinity and specificity (Mrksich, M., Parks, M. E. and Dervan, P. B. (1994) J. Am. Chem. Soc. 116: 7983). Such hairpin linked polyamides can now be synthesised efficiently and in large scale using solid phase synthesis (Baird, E. E. and Dervan, P. B. (1996) J. Am. Chem. Soc. 118: 6141–6146) and carry reactive terminal groups that could be readily coupled either directly or via a spacer group to a lipophilic domain of the current invention.

Other potential "x" groups capable of complexing with nucleic acids by the formation of hydrogen bonds other than those occurring in base pairing are exemplified by polyvinyl derivatives such as polyvinyl alcohol (PVA) and polyvinyl pyrrolidone (PVP). PVA and PVP are both capable of forming hydrogen bonds, acting as hydrogen-bond donors and acceptors respectively (Galaev. Y., Garg, N. and Mattiason, (1994) J. Chromatogr. A. 684: 45–64; Behler, V., (1993) Kollidon: Polyvinyl pyrrolidone for the pharmaceutical industry. BASF Aktiengellschaft Feinchemie, Ludwigshafen). PVP in particular has been shown to interact with DNA and protect it from nuclease attack while both PVP and PVA have been shown to enhance DNA uptake by rat skeletal muscle (Mumper, R. J., Duguid, J. G., Anwer, K., Barron, M. K., Nitta, H. and Rolland, A. P. (1996) Pharma. Res. 13:701–709). Shorter oligomers of vinyl alcohol and vinyl pyrrolidone, when coupled via a spacer moiety to a lipophilic domain, could bind nucleic acid and facilitate its uptake by cells. PVA is often produced by the hydrolysis of polyvinyl acetate with alkali. While alcohol groups of PVA or oligo VA are relatively unreactive, linkage could be achieved through reactive acetate groups on partially hydrolysed oligo VA. Using a similar rationale if PVP (or oligo VP) were produced by reacting a compound such as polyvinyl chloride (or oligovinyl chloride) with pyrrolidone, coupling to a spacer group in the current invention could be achieved through residual chloride groups on incompletely derivatized PVP (or oligo VP) product.

The spacer "y" joining the nucleic acid binding group "x" to the amino group of the linker, for example. Tris may be any of a number of molecules well known in the art. The nature of the spacer will depend on the reactive groups available on the nucleic acid binding moiety "x". Examples of spacers "y" are:

1. Between an "x" group with an amino group and the amino group of the linker.
a) a spacer with a carboxyl group to the "x" moiety and a carboxyl group to the amino group, such as dicarboxylic acids via the anhydride, e.g. succinic anhydride, maleic anhydride etc.
b) a spacer with an carboxyl group to the "x" moiety and an aldehyde group to the amino group such as glyoxylic acid (in the presence of reducing agent, e.g. $NaBH_4$) or vice versa.
c) a spacer with a carboxyl group to the "x" moiety and a halide to the amino group such as chloroacetic acid or vice versa.
d) a spacer with a halide group to "x" and a sulphonic acid group to the amino group such as 2-bromoethanesulphonic acid or vice versa.
e) a spacer with a chloroformate group to "x" and a halide group to the amino group such as bromoethyl chloroformate or vice versa.
f) a spacer with a halide group to "x" and a halide group to the amino group such as 1,2 dibromoethane.
g) other examples of potentially suitable spacers between an "x" group with an amide group and the amino group include the compound families exemplified by acrylic acid.

2. Between an "x" group with an hydroxyl group and the amino group of the linker.
a) a spacer with a carboxyl group to the "x" group and a carboxyl group to the amino group, such as dicarboxylic acids via the anhydride, e.g. succinic anhydride, maleic anhydride etc.
b) a spacer with an carboxyl group to the "x" moiety and an aldehyde group to the amino group such as glyoxylic acid (in the presence of reducing agent, e.g. $NaBH_4$).
c) a spacer with a carboxyl group to the "x" moiety and a halide to the amino group such as chloroacetic acid.
d) a spacer with a carboxyl group to the "x" moiety and an N═C═O group to the amino group such as ethylisocyanatoacetate.

3. Between an "x" group with a thiol group and the amino group of the linker.
a) a spacer with a carboxyl group to the "x" group and a carboxyl group to the amino group, such as dicarboxylic acids via the anhydride, e.g. succinic anhydride, maleic anhydride etc.
b) a spacer with an carboxyl group to the "x" moiety and an aldehyde group to the amino group such as glyoxylic acid (in the presence of reducing agent, e.g. $NaBH_4$).
c) a spacer with a carboxyl group to the "x" moiety and a halide to the amino group such as chloroacetic acid.
d) a spacer with a carboxyl group to the "x" moiety and an N═C═O group to the amino group such as ethylisocyanatoacetate.

4. Between an "x" group with a free carboxyl group and the amino group of the linker.
a) a spacer with an amino group to the "x" moiety and a carboxyl group to the amino group e.g. an amino acid or an antibiotic.
b) a spacer with an amino to the "x" moiety and a sulphonic acid group to the amino group e.g. 2- aminoethanesulphonic acid (taurine).

c) a spacer with an hydroxyl to the "x" moiety and a carboxyl group to the amino group e.g. glycolic acid, lactic acid etc.

d) a spacer with an hyroxyl group to the "x" and a sulphonic acid group to the amino group e.g. 2-hydroxyethanesulphonic acid.

e) a spacer with an hydroxyl group to the "x" moiety and a reactive halide to the amino group e.g. 2-chloroethanol.

f) other examples of potentially suitable spacers between a compound with a reactive carboxyl and the amino group include compound families exemplified by p-hydroxybenzaldehyde, 2-chloroacetic acid, 1,2-dibromomethane and ethyleneoxide.

As is clear from the above description the spacer "y" may be absent, however, it is preferred that the molecule does include spacer "y". As state above the spacer may be any of a number of molecules well known in the art. It is, however, presently preferred that the spacer has a chain length equivalent to 3 to 17 carbon atoms. In this regard it is particularly preferred that the spacer is amino butyric, amino caproic, amino caprylic, amino undecanoic acid or a dipeptide of amino caproic acid and amino undecanoic acid.

In a preferred embodiment of the present invention $R_1$, $R_2$ and $R_3$ are alkyl, hydroxy alkyl or alkenyl groups. Preferred alkyl groups are derived from 1-bromo undecane, 1-bromotridecane or 1-bromo hexadecane. Preferred hydroxy alkyl groups are derived from 11-bromo-1-undecanol, 13-bromo-1-tridecanol or 16-bromo-1-hexadecanol. Preferred alkenyl groups are derived from 7-dodecene-1-, 11-tetradecene-1-, 11-hexadecene-1-or oleyl p-toluenesulfonate. These groups may be coupled to the linker via an ether linkage.

In a further preferred embodiment $R_1$, $R_2$ and $R_3$ are acyl groups and have a carbon chain length of 3–24 carbon atoms saturated or unsaturated. These groups may be coupled to the linker by ester linkages involving the acyl group.

In yet a further preferred embodiment of the present invention $R_1$, $R_2$ and $R_3$ are the same, and are preferably cholesterol or acyl derivatives of fatty acids including the group consisting of palmitate, myristate, laurate, caprate and oleate.

While the compound is depicted as using tromethamine to couple the spacer (and through this the nucleic acid binding domain and thence the nucleic acid itself) to 1–3 lipophilic groups, it will be apparent to those skilled in the art that a similar coupling could also be effected through an ethanolamine derivative where it is desired to use only one acyl derivative of fatty acids.

Accordingly, in a third aspect the present invention consists in a method for introducing nucleic acid into a cell comprising exposing the cell to a compound having the formula:

w . . . x—y—NH—CH$_2$—CH$_2$O—R$_5$ in which:

w is a nucleic acid x is a non-amino acid or non-peptide nucleic acid binding group y is a spacer having a chain length equivalent to 1–30 carbon-carbon single covalent bonds or is absent $R_5$ is alkyl, alkenyl, hydroxylated alkyl, hydroxylated alkenyl group or ether containing alkyl, alkenyl, hydroxylated alkyl or hydroxylated alkenyl group, optionally being an acyl group derived from a fatty acid having a carbon chain length equivalent to3–24 carbon atoms saturated or unsaturated, with the proviso that $R_5$ includes a group having a carbon chain of 3–24 carbon atoms saturated or unsaturated.

In a fourth aspect the present invention consists in a compound for use in introducing nucleic acid into a cell, the compound having the formula:

w . . . x—y—NH—CH$_2$—CH$_2$O—R$_5$ in which:

w is a nucleic acid x is a non-amino acid or non-peptide nucleic acid binding group y is a spacer having a chain length equivalent to 1–30 carbon-carbon single covalent bonds or is absent $R_5$ is alkyl, alkenyl, hydroxylated alkyl, hydroxylated alkenyl group or ether containing alkyl, alkenyl, hydroxylated alkyl or hydroxylated alkenyl group, optionally being an acyl group derived from a fatty acid having a carbon chain length equivalent to 3–24 carbon atoms saturated or unsaturated, with the proviso that $R_5$ includes a group having a carbon chain of 3–24 carbon atoms saturated or unsaturated.

The method and the compounds of the present invention may be used for the delivery of nucleic acids including DNA, RNA, oligonucleotides (either wholly DNA or RNA or chimaeras thereof) and modified oligonucleotides into eucaryotic cells in culture including established cell lines of animal or plant origin and primary cells of animal or plant origin. With regard to delivery to plant cells and mammalian cell lines, reference is made to EPO424688, the disclosure of which is incorporated herein by reference. As plants can be regenerated from protoplasts in culture the method also provides for the production of whole plants containing the delivered nucleic acids. It can also be used to introduce such nucleic acids into whole animals. The introduction into a mammalian host may be by any of several routes including by not limited to intravenous or intraperitoneal injection, intratracheally, intrathecally, parenterally, intraarticularly, intramuscularly, etc.

The method of the present invention is generally envisaged to involve the application of the composition in an essentially aqueous mixture to the surface of the cells of interest. However, in the case of whole organisms it may be necessary to apply the composition in an essentially non-aqueous form, by localised or systemic injection, topically or by inhalation.

The lipid delivery agents can comprise multilamellar vesicles (MLVs), small unilamellar vesicles (SUVs), large unilamellar vesicles (LUVs) or related structures. To prepare LUV and MLV aqueous material is mixed with the dry lipid film and vortexed rather than sonicated. Extrusion of these mixtures through sized polycarbonate filters can produce delivery particles of more uniform size. SUVs can be prepared by extended sonication of MLVs so producing a homogeneous population of unilamellar delivery particles. Commonly used methods for making lipid delivery particles include ether injection (Deamer, D. and Bangham, A., Biochim. Biophys. Acta (1976) 443: 629; Ostro, et al., Biochem. Biophys. Res. Commun. (1977) 76: 836; Fraley, et al., Proc. Natl. Acad. Sci. U.S.A. (1979) 76: 3348); $Ca^{2+}$-EDTA chelation (Papahadjopoulos, et al., Biochim. Biophys. Acta (1975) 394: 483; Wilson, et al., Cell (1979) 17; 77) detergent dialysis (Enoch, H. and Strittmatter. P., Proc Natl. Acad Sci. U.S.A. (1979) 76: 145 and reverse phase evaporation (REV) (Fraley, et al., J. Biol Chem. (1980) 225: 10431; Szoka, F. and Papahadjopoulos, D., Proc. Natl. Acad. Sci. U.S.A. (1978) 75: 145; Schaefer-Ridder, et al., Science (1982) 215: 166). Other methods for preparing vesicular structures formed from cationic peptide/fatty acyl conjugates and suitable for transfection are also described in PCT/AU95/00505 which is incorporated herein by reference.

To enable the formation of cationic liposomes under appropriate conditions it may be necessary to include the addition of neutral lipids. It is believed that formulation of the invention into liposomes by standard methods with a neutral lipid such as phosphatidylcholine, phosphatidylethanolamine, dioleoylphosphatidylethanolamine (DOPE), DOPC (DOP choline) or cholesterol will increase the capacity of the invention to facilitate delivery of compounds into cells. This is particularly likely where the number of lipophilic groups of the invention is 2. Methods for formulating liposomes are described, for example, in Felgner, P. L. et al. (1987) Proc. Natl. Acad. Sci. (U.S.A.) 84: 7413–7417; Yago, K et al. (1993) Biochem. Biophys. Res. Comm. 196: 1042–1048 and Campbell, M. J. (1995) Biotechniques 18:1027.

A major application of this invention would be as a gene therapy delivery agent where it would be expected to facilitate nucleic acid uptake by cells either ex vivo (with subsequent return of the genetically manipulated cells to the body) or in vivo (with direct uptake of nucleic acid by the tissues of a patient). Further information regarding gene therapy may be found in Nabel et al., (1993) Proc. Natl. Acad. Sci. U.S.A. 90: 11307–11311, the disclosure of which is incorporated herein by reference. The invention would also be expected to find important application in the production of transgenic animals and plants, genetic immunization (facilitating improved uptake and expression of nucleic acids encoding the desired antigen by the cells of the tissue to which the nucleic acid/delivery compound complexes are applied, with a subsequent immune response being raised to the expressed antigen) and gene replacement via homologous recombination.

Using this method a wide range of possible amphiphilic conjugates having 1–3 lipophilic groups can be formed. In order that the nature of the present invention might be more clearly understood, example syntheses of lead compounds will now be described in addition to the methods for assessing their transfecting activity.

Chemical Synthesis
Abbreviations used:
DCC=Dicyclohexylcarbodiimide
DMF=Dimethylformamide
HOSU=N-Hydroxysuccinimide
HPLC=High performance liquid chromatography
Suc=succinic acid
Tris=2-Amino-2-hydroxy-methyl-1,3 propanediol, tromethamine

EXAMPLE 1

METHOD FOR PREPARATION OF SPERMINE-SUC-TRIS-MONO, DI, AND TRILAURATE

Preparation of Benzyl-Suc-Tris

Succinic acid can be protected with benzyl alcohol in the presence of DCC to obtain mono benzyl succinic acid. The product can then be purified via silica gel chromatography. Mono benzyl succinic acid can then be activated with HOSU in the presence of DCC. The title product can then be obtained by coupling of the above activated ester with tris.

Preparation of 2,3,4-tri-N-BOC-Spermine

This compound can be synthesised by repetition of a three step sequence; (i) Michael addition of a diamine to acrylonitrile; (ii) BOC protection and (iii) lithium aluminium hydride reduction according to the literature reported by Goodnow et al., (1990) Tetrahedron 46: 463267–3286.

Preparation of 1-N-Suc-Tris,2,3,4-tri-N-BOC-Spermine

Benzyl-Suc-Tris can be deprotected by hydrogenolysis in the presence of palladium/carbon. The free carboxyl group can then be activated with HOSU in the presence of DCC and then coupled to the 1-N group of the 2,3,4 tri-N-BOC-Spermine to obtain the title product.

Preparation of Spermine 1-N-Suc-Tris, mono, di, and trilaurate

1-N-Suc-Tris, 2,3,4-tri-N-Boc-Spermine was reacted with lauric acid in the presence of DCC to give a mixture of the title compound following removal of the three BOC group with TFA. The three compounds can then be separated by silica gel chromatography with elution by organic solvents.

Other analogs with different length of the polyamine, different kind of spacer and fatty acyl groups can be synthesised according to the method described above with slight modification as required.

EXAMPLE 2

METHOD FOR PREPARATION OF DNA-TRIS-MONO, DI, AND TRILAURATE CONJUGATES WITH AN AMINOSPACER EITHER IN THE 3' OR 5' TERMINUS

Preparation of thioglycolate—mono, di, and trilaurate

Thioglycolic acid can be activated with HOSU in the presence of DCC. The activated ester can then be coupled to Tris in a DMF solution. It can then be purified by extraction with ethyl acetate. This product can then by acylated with lauric acid in the presence of DCC to give a mixture of the title products. The three compounds can then be separated by silica gel chromatography with elution by organic solvents.

Preparation of DNA-iodo-acetyl

Iodoacetic acid can be activated with HOSU in the presence of DCC. This activated ester can then be coupled to the aminospacer in the 3' or 5' terminus of the DNA; an aminospacer group can be attached to DNA either on 3' or 5' end by commercially available aminolink reagent. The product can then be purified on an anion-exchange column.

Preparation of DNA-acetyl-glycolate-Tris-laurate

The DNA-iodo-acetyl can be coupled specifically to the thiol group of the thioglycol-laurate immediately after preparing the DNA iodo acetyl. The product can then be purified by reverse phase HPLC.

EXAMPLE 3

METHOD FOR PREPARATION OF DNA-TRIS-MONO, DI, AND TRILAURATE CONJUGATES WITH A PHOSPHORAMIDITE SPACER IN THE 5' TERMINUS OF THE DNA

Preparation of Benzyl-Suc-Tris-mono, di, and trilaurate

Succinic acid can be protected with benzyl alcohol in the presence of DCC to obtain mono benzyl succinic acid. The product can then be purified via silica gel chromatography. Mono benzyl succinic acid can then be activated with HOSU in the presence of DCC and then coupled to Tris to obtain benzyl-succinate. This compound can then be acylated with lauric acid in the presence of DCC to give a mixture of the title compound. The three compounds can then be separated by silica gel chromatography with elution by organic solvents.

Preparation of Hexanol-Suc-Tris-mono, di, and trilaurate

The benzyl group on the benzyl-succinate-trilaurate can be removed with hydrogenolysis in the presence of Palladium/carbon. This product can then be activated with HOSU in the presence of DCC and then coupled to the amino group of aminohexanol to obtain the title compound. The free hydroxyl group of the mono and dilaurate conjugates can be protected with dimethyoxy trityl before deprotection of the benzyl group to avoid further reactions of these free hydroxyl groups in the next reaction.

Preparation of O-methoxy diisopropylaminophosphinyl-Hexanol-Suc-Tris-mono, di, and trilaurate The hydroxyl group of the hexanol can be reacted with N,N, diisopropylmethyl phosphonamidic chloride to give the title compound in high yields. The product can then be purified by silica gel chromatography.

Preparation of DNA-Tris-laurate conjugates

The O-methoxy diisopropylaminophosphinyl-Hexanol-Suc-Tris-mono, di, or trilaurate can be used like a phosphoramidite nucleoside and can be coupled to the 5' hydroxyl terminus of the support bound DNA in the final coupling cycle of an automated oligonucleotide synthesis. Ammonia cleavage and deprotection can give the fatty acid-DNA conjugate in solution.

Assessment of Transfection Properties
Abbreviations used:
β-Gal=β-galactosidase (from $E.\ coli$)
CAT=Chloramphenicol Acetyl Transferase
CHO=Chinese Hamster Ovary cells
Cos1=African Green Monkey kidney cells carrying the large T antigen from SV40 virus.
DME=Dulbecco's Modified Eagles medium
DMSO=Dimethylsulphoxide
DPBS=Dulbecco's Phosphate Buffered Saline
EMEM=Earl's Modified Eagles Medium
FCS=Foetal Calf Serum
h=hours
lac Z=gene encoding $E.\ coli$ β-galactosidase
MTS=3-(4,5-dimethylthiazol-2-yl)-5-(3-carboxymethoxyphenyl)-2-(4-sulphophenyl)-2H-tetrazolium, inner salt
PBS=Phosphate Buffered Saline
PMS=Phenazine methosulphate
PGK=Phosphoglycerate Kinase
X-Gal=5-Bromo-4-chloro-3-indolyl-β-D-glactopyranoside

COMPOUNDS AND EXPRESSION CASSETTES

A lead compound, SpSucTL3 (spermine-succinic acid spacer—trilaurate), was designed. It would be expected to attract DNA by virtue of its overall positive charge. It would be insoluble in aqueous solution, but soluble in both ethanol and DMSO. When a 10 mM stock solution prepared in ethanol or DMSO is diluted in sterile water with vortexing to provide a 2 mM working solution, the compound would spontaneously form vesicles which remain in suspension for at least 1 month when stored at 4° C. In the presence of nucleic acid the vesicles would be expected to fuse around these polyanionic molecules providing a lipid coating that will facilitate their cellular uptake (Gershon. H. et al., (1993) Biochemistry 32: 7143).

To test the transfection properties of the lead compound SpSucTL3, whole uncut plasmid carrying a reporter gene expression cassette, e.g. the CAT gene under the control of the SV40 late promoter (pSVLCAT) (Cameron, F. H. and Jennings, P. A. (1989) Proc. Natl. Acad, Sci. U.S.A. 86, 9139–9143) or the β-Gal gene under the control of either the mouse PGK promoter (pPGKlacZNLS) (gift of Dr. G. N. Hannan) or the SV40 early promoter (pSVGAL) (Sleight, M. J. and Lockett, T. J. (1985). EMBO J. 4: 3831–3837) can be used. After 48 h of culture the level of reporter gene product present in the cells can be measured.

TRANSFECTION

For experiments where the level of reporter gene product (in this example β-Gal activity) is used as the measure of transfection efficiency, each well in an 8×9 array of wells in a microtitre dish would be seeded with the cells to be transfected (e.g. $2 \times 10^4$ Cos1 cells or $1 \times 10^4$ CHO cells) in an appropriate culture medium (e.g. EMEM or DME), 10% FCS and allowed to adhere overnight. The next day, in a new microtitre tray, a DNA dilution plate would be set up by placing 250 μl of DME containing 4.0 μg of β-Gal plasmid in each of the top nine wells of the plate. DME (125 μl) would be added to the seven rows of nine wells immediately below the DNA containing wells. The DNA would then be serially diluted in two fold steps through the seven rows of medium-containing wells resulting in a plate with eight rows of wells in which all wells of any given row carried an identical amount of DNA. In an analogous way, a transfection agent dilution plate would also be prepared. To eight wells of the left most column of a new microtitre plate would be added 120 μl of DME containing the transfection reagent ((poly)cation- (e.g. SpSucTL3) or nucleic acid-spacer—lipophilic conjugate or other control cationic lipid-based delivery agent e.g. the commercially available reagents Lipofectamine, DOTAP or Transfectam) at 168 μM. To eight wells of the adjacent eight columns of wells would be added 60 μl of DME. The transfection reagent would then be serially diluted in two-fold steps through the columns of medium-containing wells resulting in nine columns of wells in which all wells of any given column contained identical concentrations of the transfection reagent to be tested. The DNA and transfection reagent dilution matrices would then be superimposed by transferring 60 μl of DNA containing medium from the wells of each row of the DNA dilution plate to the corresponding row of the transfection reagent plate. This plate may then be shaken for 1 min to thoroughly mix the DNA and reagent then either applied directly to the cells (see below) or allowed to stand at room temperature for 5–30 min to facilitate formation of the transfection complex prior to application to cells. Cells would be washed once with DME then the transfection matrix would be transferred to the cell plate, 100 μl of the appropriate DNA/reagent mix per well. Plates would then be incubated for 4 h at 37° C., 95% humidity in 5% $CO_2$. DME, 10–20% FCS (100 μl) would then be added to each well and the plates incubated for 48 hours. Optionally the DNA/reagent complexes can be prepared at double the concentration in 50 Tl of serum free medium and added to cells that remain in 50 Tl of medium containing an appropriate FCA (typically 5–10%). This is particularly useful for cell types that cannot tolerate the absence of serum for the period of the transfection.

In transfection experiments where the level of CAT activity produced by cells after transfection is used as the measure of transfection efficiency, solution I (1 μg of plasmid DNA in 500 μl DME) is added to solution II (0–20 Tl transfection reagent ((poly)cation- or nucleic acid-spacer—lipophilic conjugate at 2.5 mg/ml in 25% DMSO or commercial transfection reagent as supplied in 500 Tl DME) and vortexed. The mixture would be allowed to stand at room temperature for 10–15 min. Cells, seeded the previous day in DME, 10% FCS at $2 \times 10^5$ per 60 mm culture dish for Cos1 cells ($1 \times 10^5$ per dish for CHO cells) and cultured overnight at 37° C., 95% humidity in a 5% $CO_2$ atmosphere, would be washed 2× with serum free DME then the appropriate mixture added to each dish. Cells would then be incubated a further 4–6 h at 37° C., 95% humidity in 5% $CO_2$. After this time the mixture would be replaced with 2 ml of DME, 10% FCS and incubated for the remaining of the 42–44 h. Where reporter gene activity (and hence transfection) is to be measured by assaying the amount of reporter product secreted into the medium, an appropriate aliquot of medium would be removed after the post-transfection incubation period and before assessment of cell viability (vide infra).

ANALYSIS OF TOXICITY

As a part of each transfection study, toxicity of the test compound in combination with nucleic acid would be tested by either the Alamar Blue or MTS assay prior to assaying reporter gene expression.

For the Alamar Blue assay (Alamar Biosciences Inc., Sacramento Calif.) the medium is removed from the cells 48 h after transfection. The medium is replaced with an appropriate volume of fresh medium containing 0.1 volumes of Alamar blue reagent. A similar addition is made to control plates or wells containing either no cells (complete toxicity control) or untransfected cells (100% survival control). Cell cultures are then incubated a further 2 h under normal conditions (37° C. and 5% $CO_2$). Where cultures are in microtitre plates in 100 µl of medium, the difference between the $A_{570}$ (test) and $A_{600}$ (reference) readings for each sample and controls can be determined using a plate reader. The resulting data give a measure of cell viability. Where larger wells or plates are used, 100 µl aliquots of Alamar blue-containing medium can be transferred from the cultures after incubation to wells of a 96 well plate and the viability again assessed using the plate reader.

For the MTS assay, (Promega) MTS (2 mg/ml in DPBS) and PMS (0.92 mg/ml in DPBS) are mixed fresh at a ratio of 20:1 and 20 µl of this mix is added to each test and control well or plate per 100 µl of culture medium. Cultures are then incubated for a further 1–2 h under normal conditions (37° C., 95% humidity and 5% $CO_2$). Where cultures are in microtitre plates in 100 Tl of medium, the difference between the $A_{490}$ (test) and $A_{655}$ (reference) readings for each sample and controls can be determined using a plate reader. Where larger wells or plates are used, 100 µl aliquots of MTS/PMS containing medium can be transferred from the cultures (after incubation) to the wells of a 96 well plate and absorbances again determined using the plate reader. The resulting data give a measure of cell viability.

MEASURING TRANSFECTION ACTIVITY VIA REPORTER GENE ACTIVITY

To measure reporter gene activity Alamar Blue- or MTS-containing medium is first removed and the cells washed 1× with PBS. For the β-Gal assay, the washed cells are lysed by the addition of 50 µl of lysis buffer (0.1% Triton X-100, 250 mM pH 8.0). Plates are sealed, frozen at −70° C., thawed and 50 µl of PBS, 0.5% BSA added to each well. To quantify β-Gal activity, 150 µl of substrate in buffer (1 mg/ml chlorophenol red galactopyranoside (Boehringer Mannheim) in 60 mM sodium phosphate buffer pH 8.0 1 mM $MgSO_4$, 10 mM KCl, 50 mM 2-mercaptoethanol) is added to each well and colour allowed to develop at room temperature for 1 min to 24 h. Activity is determined by reading the $A_{570}$ for each well relative to those produced by known set of β-Gal standards. For CAT assays the method described by Sleigh (Sleigh, M. J. (1986) Anal. Biochem., 156: 251–256) can be used.

An alternative way to examine transfection efficiency is to determine the proportion of cells transfected by different reagents. This can be achieved by transfecting cells with plasmids containing reporter gene (e.g. lac Z) expression cassettes under conditions similar to those described above for the CAT experiments, with the exception that the cells are grown in the wells on coverslips. Cells are then fixed and treated with a chromogenic substrate for the β-Gal enzyme.

After the viability analysis, the cells are washed 2× in PBS then fixed for 5 min at 4° C. in 0.2% glutaraldehyde in 0.1M phosphate buffer, pH 7.3. Cells are washed 2× with cold PBS. Fresh staining solution (10 ml 0.1M phosphate buffer, pH 7.3; 1.0 ml of a 1:1 mix of 105 mg potassium ferrocyanide in 2.5 ml $H_2O$ and 82 mg of potassium ferricyanide in 2.5 ml $H_2O$; 0.2 ml of 2% X-gal in dimethylformamide, 11.2 µl of 1M $MgSO_4$) (2 ml) is added to each dish and the dishes incubated at 37° C. until colour develops. Random fields of cells are examined by light microscopy and the proportion of blue (β-Gal-expressing) cells can be determined.

In addition to delivering nucleic acids containing gene expression cassettes the transfection reagents of this invention can be used to deliver oligonucleotides (whether composed of RNA, DNA, protected nucleotides or combination of these) into cells. The efficiency with which transfection reagents can deliver such nucleic acids to cells can be determined by labelling the oligonucleotides by any of a number of methods well known in the art including, but not limited to, using radioactivity, fluorescent tags, biotin and digoxigenin. By way of example, where the proportion of cells transfected with oligonucleotide using a particular reagent is measured using fluoresceinated oligonucleotides, the conditions for transfection would be similar to those described above for the CAT experiments. Briefly, $8 \times 10^4$ Cos1 cells ($5 \times 10^4$ CHO cells) would be seeded onto coverslips in the wells of a 24 well plate in DME, 10% FCA and incubated at 37° C. in 5% $CO_2$/air to allow cell attachment. A Fluoresceinated oligonucleotide (20 µM in 250 µl of DME) would be mixed with transfection reagent (SpSucTL3 or Lipofectamine, 0.25, 0.5 or 1 µl of a 2 mM stock in 250 µl of DME) and allowed to stand at room temperature for 15–30 min. Cells would then be washed 1× with DME and 500 µl of the different transfection mixes would be added to the wells. Plates would then be incubated at 37° C., 95% humidity in 5% $CO_2$ for 4 h. After incubation the medium would be removed and the cells washed 1× with PBS. Cover slips would be removed from the wells, mounted in PBS and examined by confocal scanning laser microscopy to score the proportion of cells containing the fluorescent label.

It will be appreciated by persons of moderate skill in the art that numerous variation and/or modifications may be made to the invention as shown in the specific embodiments without departing from the spirit and scope of the invention as broadly described.

We claim:

1. A method for introducing nucleic acid into a cell comprising exposing the cell to a compound having the formula:

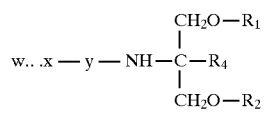

in which:
w is a nucleic acid
x is a non-amino acid or non-peptide binding group y is a spacer having a chain length equivalent to 1–30 carbon-carbon single covalent bonds or is absent $R_4$ is H or halogen or $CH_2O$—$R_3$; and $R_1$, $R_2$ and $R_3$ are the same or different and are either hydrogen, methyl, ethyl, alkyl, alkenyl, hydroxylated alkyl, hydroxylated alkenyl groups or ether containing alkyl, alkenyl, hydroxylated alkyl or hydroxylated alkenyl groups, optionally being an acyl group derived from a fatty acid having a carbon chain length equivalent to 3–24 carbon atoms saturated or unsaturated, with the proviso that at least one of $R_1$, $R_2$ or $R_3$ includes a group having a carbon chain of 3–24 carbon atoms saturated or unsaturated.

2. A method as claimed in claim 1 in which y is present.

3. A method as claimed in claim 1 in which the nucleic acid is DNA, RNA or oligonucleotides of either DNA or RNA, modified oligonucleotides or a combination thereof.

4. A method as claimed in claim 1 in which $R_1$, $R_2$ and $R_3$ are the same.

5. A method as claimed in claim 1 in which $R_1$, $R_2$ and/or $R_3$ are cholesterol or acyl derivatives of fatty acids selected from the group consisting of palmitate, myristate, laurate, caprate and oleate.

6. A method as claimed in claim 5 in which $R_1$, $R_2$ and/or $R_3$ are acyl derivatives of myristate or laurate.

7. A method as claimed in any claim 1 in which the cells are animal cells.

8. A method as claimed in claim 1 in which the cells are plant cells.

9. A method as claimed in claim 7 in which the method is conducted in vitro.

10. A method as claimed in claim 7 in which the method is conducted in vivo.

11. A method as claimed in claim 10 in which the compound is administered topically, intravenously, intramuscularly, by inhalation, injection, orally or by suppository.

12. A method as claimed in claim 1 in which the compound is present in a liposome or mixed with another lipid.

13. A method as claimed in claim 1 in which the compound contains a spacer group "y" having a chain length equivalent to 3 to 17 carbon atoms.

14. A method as claimed in claim 13 in which y is amino butyric, amino caproic, amino caprylic or amino undecanoic acid or a dipeptide of amino caproic acid and amino undecanoic acid.

15. A method as claimed in claim 1 in which x has an overall positive charge and the nucleic acid is associated electrostatically.

16. A method as claimed in claim 1 in which x is an oligonucleotide and nucleic acid w is associated with x by base pairing or triple helix formation.

17. A method as claimed in claim 1 in which w is covalently attached to x.

18. A method as claimed in claim 1 in which w is associated to x by hydrogen bonding.

19. A method for introducing nucleic acid into a cell comprising exposing the cell to a compound having the formula:

w . . . x—y—NH—$CH_2$—$CH_2$O—$R_5$ in which:

w is a nucleic acid x is a non-amino acid or non-peptide binding group y is a spacer having a chain length equivalent to 1–30 carbon-carbon single covalent bonds or is absent $R_5$ is alkyl, alkenyl, hydroxylated alkyl, hydroxylated alkenyl group or ether containing alkyl, alkenyl, hydroxylated alkyl or hydroxylated alkenyl group, optionally being an acyl group derived from a fatty acid having a carbon chain length equivalent to 3–24 carbon atoms saturated or unsaturated, with the proviso that $R_5$ includes a group having a carbon chain of 3–24 carbon atoms saturated or unsaturated.

20. A method as claimed in claim 19 in y is present.

21. A method as claimed in claim 19 in which the nucleic acid is DNA, RNA or oligonucleotides of either DNA or RNA, modified oligonucleotides or a combination thereof.

22. A method as claimed in claim 19 in which $R_5$ is cholesterol or an acyl derivative of a fatty acids selected from the group consisting of palmitate, myristate, laurate, caprate and oleate.

23. A method as claimed in claim 22 in which $R_5$ is an acyl derivative of myristate or laurate.

24. A method as claimed in claim 19 in which the cells are animal cells.

25. A method as claimed in claim 19 in which the cells are plant cells.

26. A method as claimed in claim 24 in which the method is conducted in vitro.

27. A method as claimed in claim 24 in which the method is conducted in vivo.

28. A method as claimed in claim 27 in which the compound is administered topically, intravenously, intramuscularly, by inhalation, injection, orally or by suppository.

29. A method as claimed in claim 19 in which the compound is present in a liposome or mixed with another lipid.

30. A method as claimed in claim 19 in which the spacer group "y" has a chain length equivalent to 3 to 17 carbon atoms.

31. A method as claimed in claim 30 in which y is amino butyric, amino caproic, amino caprylic or amino undecanoic acid or a dipeptide of amino caproic acid and amino undecanoic acid.

32. A method as claimed in claim 19 in which x has an overall positive charge.

33. A method as claimed in claim 19 in which x is an oligonucleotide and nucleic acid w is associated with x by base pairing or triple helix formation.

34. A method as claimed in claim 19 in which w is covalently attached to x.

35. A method as claimed in claim 19 in which w is associated to x by hydrogen bonding.

36. A compound for use in introducing nucleic acid into a cell, the compound having the formula

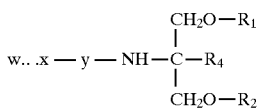

in which:

w is a nucleic acid x is a non-amino acid or non-peptide binding group y is a spacer having a chain length equivalent to 1–30 carbon-carbon single covalent bonds or is absent $R_4$ is H or halogen or $CH_2O$—$R_3$; and $R_1$, $R_2$ and $R_3$ are the same or different and are either hydrogen, methyl, ethyl, alkyl, alkenyl, hydroxylated alkyl, hydroxylated alkenyl groups or ether containing alkyl, alkenyl, hydroxylated alkyl or hydroxylated alkenyl groups, optionally being an acyl group derived from a fatty acid having a carbon chain length equivalent to 3–24 carbon atoms saturated or unsaturated, with the proviso that at least one of $R_1$, $R_2$ or $R_3$ includes a group having a carbon chain of 3–24 carbon atoms saturated or unsaturated.

37. A compound as claimed in claim 36 in which y is present.

38. A compound as claimed in claim 36 in which w is DNA, RNA or oligonucleotides of either DNA or RNA, modified oligonucleotides or a combination thereof.

39. A compound as claimed in claim 36 in which $R_1$, $R_2$ and $R_3$ are the same.

40. A compound as claimed in claim 36 in which $R_1$, $R_2$ and/or $R_3$ are cholesterol or acyl derivatives of fatty acids selected from the group consisting of palmitate, myristate, laurate, caprate and oleate.

41. A compound as claimed in claim 40 in which $R_1$, $R_2$ and/or $R_3$ are acyl derivatives of myristate or laurate.

42. A compound as claimed in claim 36 in which the compound is present in a liposome or mixed with another lipid.

43. A compound as claimed in claim 36 in which the compound contains a spacer group "y" having a chain length equivalent to 3 to 17 carbon atoms.

44. A compound as claimed in claim 43 in which y is amino butyric, amino caproic, amino caprylic or amino undecanoic acid or a dipeptide of amino caproic acid and amino undecanoic acid.

45. A compound as claimed in claim 36 in which x has an overall positive charge.

46. A compound as claimed in claim 36 in which x is an oligonucleotide and nucleic acid w is associated with x by base pairing or triple helix formation.

47. A compound as claimed in claim 36 in which w is covalently attached to x.

48. A compound as claimed in claim 36 in which w is associated to x by hydrogen bonding.

49. A compound for use in introducing nucleic acid into a cell, the compound having the formula:

w . . . x—y—NH—$CH_2$—$CH_2$O—$R_5$ in which:

w is a nucleic acid x is a non-amino acid or non-peptide binding group y is a spacer having a chain length equivalent to 1–30 carbon-carbon single covalent bonds or is absent $R_5$ is alkyl, alkenyl, hydroxylated alkyl, hydroxylated alkenyl group or ether containing alkyl, alkenyl, hydroxylated alkyl or hydroxylated alkenyl group, optionally being an acyl group derived from a fatty acid having a carbon chain length equivalent to 3–24 carbon atoms saturated or unsaturated, with the proviso that $R_5$ includes a group having a carbon chain of 3–24 carbon atoms saturated or unsaturated.

50. A compound as claimed in claim 49 in which y is present.

51. A compound as claimed in claim 49 in which w is DNA, RNA or oligonucleotides of either DNA or RNA, modified oligonucleotides or a combination thereof.

52. A compound as claimed in claim 49 in which $R_5$ is cholesterol or an acyl derivative of a fatty acids selected from the group consisting of palmitate, myristate, laurate, caprate and oleate.

53. A compound as claimed in claim 52 in which $R_5$ is an acyl derivative of myristate or laurate.

54. A compound as claimed in claim 49 in which the compound is present in a liposome or mixed with another lipid.

55. A compound as claimed in claim 49 in which the compound contains a spacer group "y" having a chain length equivalent to 3 to 17 carbon atoms.

56. A compound as claimed in claim 55 in which y is amino butyric, amino caproic, amino caprylic or amino undecanoic acid or a dipeptide of amino caproic acid and amino undecanoic acid.

57. A compound as claimed in claim 49 in which x has an overall positive charge.

58. A compound as claimed in claim 49 in which x is an oligonucleotide and nucleic acid w is associated with x by base pairing or triple helix formation.

59. A compound as claimed in claim 49 in which w is covalently attached to x.

60. A compound as claimed in claim 49 in which w is associated to x by hydrogen bonding.

61. A method according to claim 1, wherein the dotted line between w and x denotes the bonding association of w and x in the compound.

62. A method according to claim 1, wherein the nucleic acid group w can associate with the non-amino acid or non-peptide group x by covalent bonding, ionic interaction, hydrogen bonding, base pairing or triplex formation.

* * * * *